United States Patent [19]

DeBonville et al.

[11] Patent Number: 4,843,012
[45] Date of Patent: * Jun. 27, 1989

[54] NOVEL COMPOSITION FOR NUCLEIC ACID PURIFICATION

[75] Inventors: David A. DeBonville, Cambridge; Gerard E. Riedel, Concord, both of Mass.

[73] Assignee: Genetics Institute, Inc., Cambridge, Mass.

[*] Notice: The portion of the term of this patent subsequent to May 23, 2006 has been disclaimed.

[21] Appl. No.: 908,413

[22] Filed: Sep. 17, 1986

[51] Int. Cl.$^4$ .......................... C12N 1/06; C12N 1/08
[52] U.S. Cl. .................................... 435/270; 435/259; 435/803
[58] Field of Search .................. 435/270, 6, 259, 803; 935/19, 20, 21

[56] References Cited

FOREIGN PATENT DOCUMENTS 0861399 9/1981 U.S.S.R. .............................. 435/270

OTHER PUBLICATIONS

Methods in Enzymology, Academic Press (N.Y.), 1980, vol. 65, pp. 404–411, 718–721.
Potter et al., Cancer Letters, 26:335–341 (1985).
Bianborin et al., Nucleic Acids Res., 7:1513–1523 (1979).

Primary Examiner—Robert J. Warden
Assistant Examiner—Randall E. Deck
Attorney, Agent, or Firm—David L. Berstein; Bruce M. Eisen; Brian P. O'Shaughnessy

[57] ABSTRACT

A storage stable single phase aqueous composition is provided which is useful in isolatin nucleic acids from cell or virus cultures.

5 Claims, No Drawings

NOVEL COMPOSITION FOR NUCLEIC ACID PURIFICATION

The present invention relates to a reagent composition useful in procedures for purifing or isolating nucleic acids from eukaryotic and prokaryotic cell and virus cultures.

BACKGROUND

In the practice of biotechnology, nucleic acid fragments are commonly isolated from prokaryotic and eukaryotic and viral culures. The isolation of these fragments enables their sequencing, their use as probes for diagnostic and other research assays, and their assembly into genes encoding whole proteins or polypeptides. Traditionally, nucleic acids have been separated from contaminating proteinaceous material (e.g., from bacterial and viral cultures) by lysis in the presence of a detergent, (e.g. sodium dodecyl sulfate) and a salt solution, (e.g., potassium acetate) followed by extraction (deproteinization) with phenol or chloroform or a mixture thereof. These procedures separate the nucleic acids, generally by precipitation, from liquid and protein contaminants of the cell or virus culture.

A well-known and often-used example of this procedure applied to the isolation of plasmid DNA from bacterial cultures is described in H. C. Birnboim and J. Doly, "A Rapid Alkaline Extraction Procedure for Screening Recombinant Plasmid DNA." *Nucleic Acids Res.* 7:1513–1523 (1979). These two steps—lysis and deproteinization—have been separately performed because the reagents in the lysis steps are not miscible with the reagents involved in deproteinization. Consequently, the lysis and deproteinization of nucleic acids from contaminants requires a two-step procedure.

INVENTION

The present invention provides a unique stable single-phase aqueous composition for use in a variety of nucleic acid isolation procedures. A reagent composition was surprisingly discovered in which the extraction components are completely soluble in the aqueous lysis components, and capable of stable combination. The present invention allows combination of the two steps of prior isolation techniques and thus simplifies the procedure for isolation of nucleic acid fragments. Unexpectedly, the novel composition of the present invention results in an increased yield of nucleic acid isolation products from the isolation techniques than does the two-step procedure.

The present invention involves a stable, single-phase aqueous composition including between 1.6M to about 3.2M potassium acetate, between about 5% to about 15% phenol by weight, between about 5% to about 15% by weight chloroform and sufficient acetic acid to provide a pH of between 6 to 9. The composition of the present invention may optionally include between 0 to about 1.2% by weight isoamyl alcohol. Alternatively, or in addition to, the alcohol is another optional ingredient, 8-hydroxyquinoline, in an amount of between 0 to 0.12% by weight.

The critical components of this composition, potassium acetate and phenol/chloroform are desiraebly in a ratio of 4 parts by weight potassium acetate to between about 1 to 3 parts by weight of the total phenol and chloroform components. The presently preferred composition has a 4 to 1 ratio thereof. In one desirable embodiment, the components of the composition are 2.4M potassium acetate, 10M acetic acid, 10% phenol, 10% chloroform, 0.2% isoamyl alcohol and 0.02% hydroxyquinoline at pH 8. A more preferred solution consists of 60 mls 5M potassium acetate, 12 mls chloroform, 40 mls acetic acid, 12 mls phenol, 1 ml isoamyl alcohol, and 0.012 grams 8-hydroxyquinoline at pH8.

A surprising facet of this reagent composition is that it alters the solubility of phenol. It is presently believed that this combination of components alters the ionic strength of the potassium acetate solution and makes the solution and the phenol miscible and stable for an indefinite period of time. The reagent composition is stable at room temperature (25° C.) for at least 30 days, and presently is stably storable for at least 60 days.

The stable composition of the present invention is useful in a variety of standard DNA isolation procedures including purifying plasmid DNA from bacterial cultures and isolating single-strand template DNA from bacteriophage M13 wherein several lysis and extraction reagents are replaced with the composition of the present invention. The reagent of the present invention may also be employed in place of standard lysis and extraction techniques known to those of skill in the art for the isolation of DNA and RNA from other tissue sources, e.g. eukaryotic cells as well as prokaryotic cells, including isolating nucleic acids from mammalian cells.

The reagent composition of the present invention may be employed in a manual DNA isolation procedure, such as described by T. Maniatis et al, *Molecular Closing—A Laboratory Manual*, Cold Spring Harbor Laboratory, (1982) or in an automated procedure, such as described in Example II below. In either type of procedure, the composition of the present invention has demonstrated an effective increase in yield of isolated nucleic acid, as well as an increase in procedural efficiency due to the combination of lytic and deproteinization functions performed by use of the reagent.

Because of its stability, this reagent composition of the present invention may be part of a kit of reagents useful in nucleic acid isolation procedures. Alternatively, the composition may be in a container useable for an automated isolation apparatus, e.g. in a container replaceably fittable to an automated isolation apparatus.

The following examples illustrates a presently preferred embodiment of the composition of the present invention and its use in an automated nucleic acid isolation procedure.

EXAMPLE I

Preparation of the Reagent Composition

A composition according to the present invention is prepared as follows.

In a first solution, 48 mls 5M potassium acetate is mixed with 32 mls glacial acetic acid (a 3:2 weight ratio of the potassium acetate to acetic acid in this solution is preferred). A second solution is formed by adding in the following order: 9.9 mls phenol, 0.1% by weight 8-hydroxyquinoline, 9.9 mls chloroform, and 0.2 mls isoamyl alcohol. These two solutions are mixed together, thereby forming a stable single phase composition of pH 8.

EXAMPLE II

Plasmid DNA Isolation from Bacterial Cells 5 mls of SOBM medium [Maniatis et al, supra p. 69] are inoculated with *E. coli* JM101 bacterial cells and M13mp19 bacteriophage and incubated overnight at 37° C. Cells are concentrated by centrifugation at a rate of 3000 rpm for ten minutes. After the medium is poured off, the resulting pellet is resuspended in 0.3 mls of 50 mM glucose, 10 mM ethylenediamine-tetraacetic acid (EDTA), and 10 mM Tris-Cl at pH 7.5 and vortexed for two minutes at room temperature. Immediately following the vortex step, 0.6 mls of 0.2N NaOH and 1% SDS is added and the solution vortexed gently at room temperature for 15 seconds, incubated for 30 seconds and vortexed gently again for 15 seconds.

To this solution, 0.54 mls of the composition of Example I is added. This mixture is gently vortexed for 15 seconds, incubated for 30 seconds, and vortexed again for 15 seconds, and then centrifuged for 15 minutes at 3000 rpm.

The resulting supernatant is transferred to a test tube having a 0.8 micron pore size cellulose acetate filter and a 5 ml receiver tube [Schliecher and Schuell]. 1.3 mls isopropanol is added to the tube and it is vortexed gently, followed by a 2 minute room temperature incubation. To bind the DNA to the filter, the contents of the tube are centrifuged for 4 minutes at 3000 rpm at room temperature. While the DNA is on the filter, 0.5 mls of 70% ethanol is added to the tube and centrifuged again for two minutes. This step is repeated three more times to insure complete removal of contaminants.

The receiver tube is then removed and replaced with a 1.5 ml, capless Eppendorf tube. 0.1 ml of a reagent solution containing 10 mM Tris-Cl at pH 8.0, 1 mM EDTA and 20 ugs/ml RNase A is added to the tube and incubated for 30 minutes at room temperature to allow the DNA to be released from the filter. The tube and its contents are then centrifuged for four minutes at 3000 rpm at room temperature.

10 μl of the resulting solution is placed in a new Eppendorf tube. 1.2 μl of 10× EcorRi buffer [New England Biolabs] is added with 1 unit of EcorRi restriction enzyme, and the resulting solution incubated for 2 hours at 37° C. The solution containing DNA fragments is analyzed by gel electrophoresis, producing linearized M13mp19 vector DNA of 7.2 kb.

When the procedure described in Maniatis et al was applied to purify the same culture, the electrophoretic gel data produced the same results as did the above procedure employing the composition of the present invention. However, the time savings caused by use of the composition of the present invention in the automated procedure was approximately 10-15 percent. Additionally, in both the manual and automated DNA plasmid isolation procedures, use of the composition of the present invention resulted in significantly higher yields of the isolated DNA fragments.

Numerous modifications to, and uses of, the composition of the present invention are expected to occur to those of skill in the art. Such modifications are believed to be encompassed by the appended claims.

What is claimed is:

1. A single phase aqueous composition that is stable against a separation of phases for at least thirty days of storage at about 25° C. and is useful in isolating nucleic acids from cell or virus cultures comprising:
   (a) about 1.6 to 3.2M potassium acetate;
   (b) about 5 to 15% by weight phenol;
   (c) about 5 to 15% by weight chloroform; and
   (d) glacial acetic acid in an amount such that the weight ratio of potassium acetate to glacial acetic acid is 3:2, wherein the weight ratio of (a) to the combination of (b) and (c) is in the range of 4:1 to 4:3.

2. The composition according to claim 1 further comprising:
   (e) 0 to about 1.2% by weight isoamyl alcohol; and
   (f) 0 to about 0.12% by weight 8-hydroxyquinoline.

3. A sealed package useful in an automated procedure for isolating DNA from cell cultures containing the stable single phase aqueous composition of claim 1.

4. In a nucleic acid isolation procedure wherein cells in a cell culture are lysed and nucleic acids are extracted from proteinaceous contaminants, the improvement comprising employing the composition of claim 1.

5. A single phase aqueous composition that is stable against a separation of phases for at least thirty days of storage at about 25° C. and is useful in isolating nucleic acids from cell or virus cultures comprising:
   (a) 2.4M potassium acetate;
   (b) 10M acetic acid;
   (c) 5 to 15% by weight phenol;
   (d) 5 to 15% by weight chloroform;
   (e) 0.2% by weight isoamyl alcohol; and
   (f) 0.02% by weight hydroxyquinoline.

* * * * *